United States Patent [19]

Jensen et al.

[11] Patent Number: 5,496,357
[45] Date of Patent: Mar. 5, 1996

[54] THERMAL BLANKET WITH ELASTIC FIT

[75] Inventors: Marvin E. Jensen, Mundelein; John A. Biewer, Winthrop Harbor, both of Ill.

[73] Assignee: Hollister Inc., Libertyville, Ill.

[21] Appl. No.: 198,613

[22] Filed: Feb. 18, 1994

Related U.S. Application Data

[63] Continuation-in-part of Ser. No. 139,286, Oct. 20, 1993.

[51] Int. Cl.$^6$ ............................................. A61F 7/00
[52] U.S. Cl. ........................... 607/108; 607/112; 607/114
[58] Field of Search ..................... 607/96, 104, 108–112, 607/114

[56] References Cited

U.S. PATENT DOCUMENTS

| | | | |
|---|---|---|---|
| 4,061,898 | 12/1977 | Murray et al. | 607/110 X |
| 4,149,541 | 4/1979 | Gammons et al. | 607/104 X |
| 4,172,495 | 10/1979 | Zebuhr et al. | 607/110 X |
| 4,575,097 | 3/1986 | Brannigan et al. | 607/112 |
| 4,805,620 | 2/1989 | Meistrell | 607/108 X |

*Primary Examiner*—Angela D. Sykes
*Attorney, Agent, or Firm*—Tilton, Fallon, Lungmus & Chestnut

[57] ABSTRACT

A thermal blanket with an elastic fit to accommodate body movement and particularly suitable for compressive postoperative thermal treatment of body joints such as the shoulder, ankle, knee, elbow, hand/wrist, back or hip, is disclosed. The blanket includes a bodyside first panel composed of double layers of thermoplastic sheet material heat-sealed together to define at least one and preferably two serpentine fluid flow passages for the circulation of cooling (or warming) fluid. The sheet material may alternatively define a relatively open passageway between an inlet and outlet. The blanket also includes a soft, foldable exterior second panel coplanar with the first panel, the edges of the two panels being secured together to form a unitary, easily-foldable blanket. The exterior panel is of soft loop-providing pile fabric over substantially the entire exterior surface thereof. The developed outline of the blanket provides at least two generally opposite or opposed free ends, one of which is provided with an elastic attachment patch having a bodyside-facing hook-providing fabric for releasable attachment to the loop-providing pile fabric of the external panel at the other or opposite free end when the blanket is wrapped about a body area for administering thermal treatment thereto. When the blanket is secured about a body area, the elasticity of the attachment patch(es) provides a snug compressive fit while still accommodating limited body movement.

9 Claims, 6 Drawing Sheets

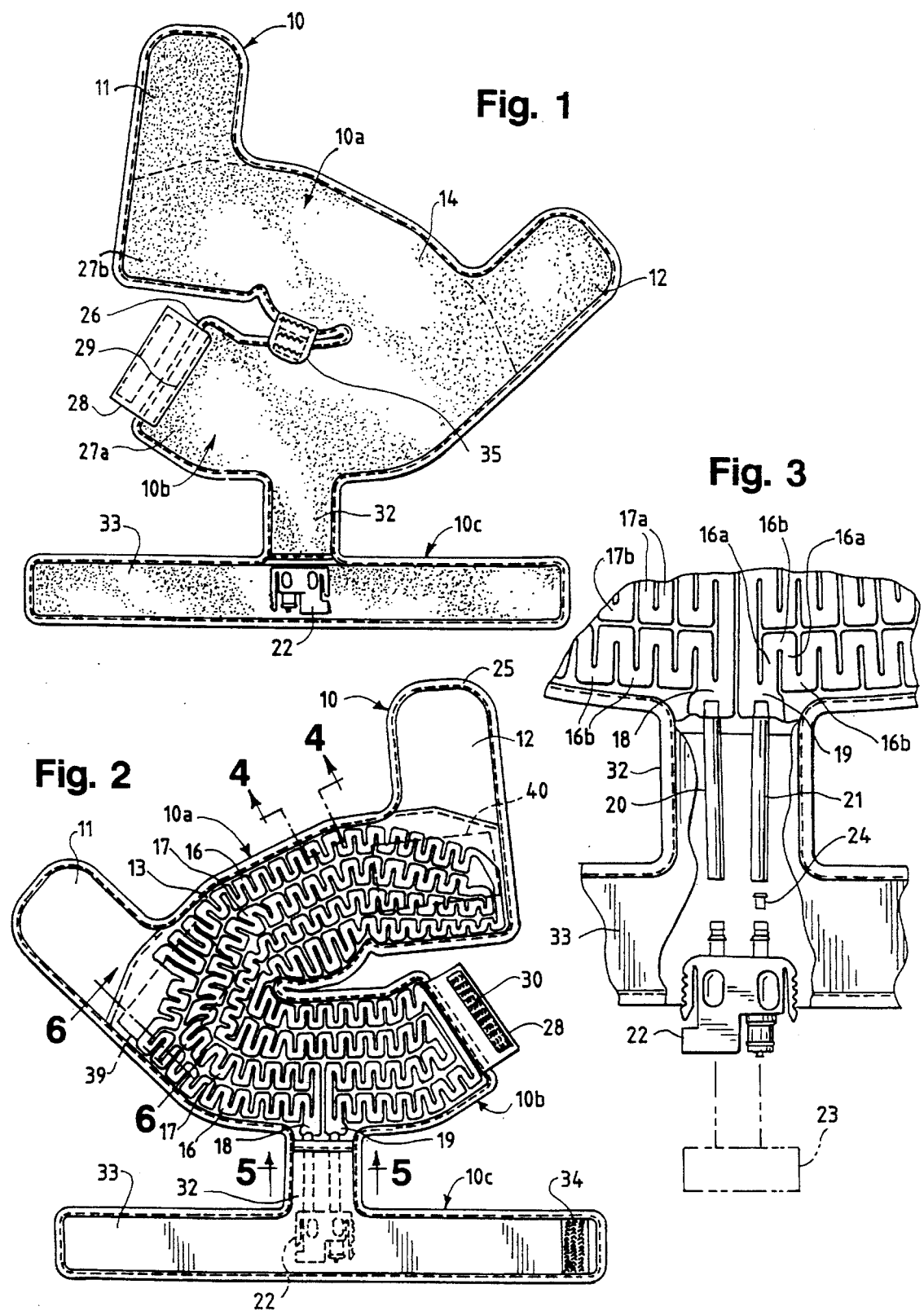

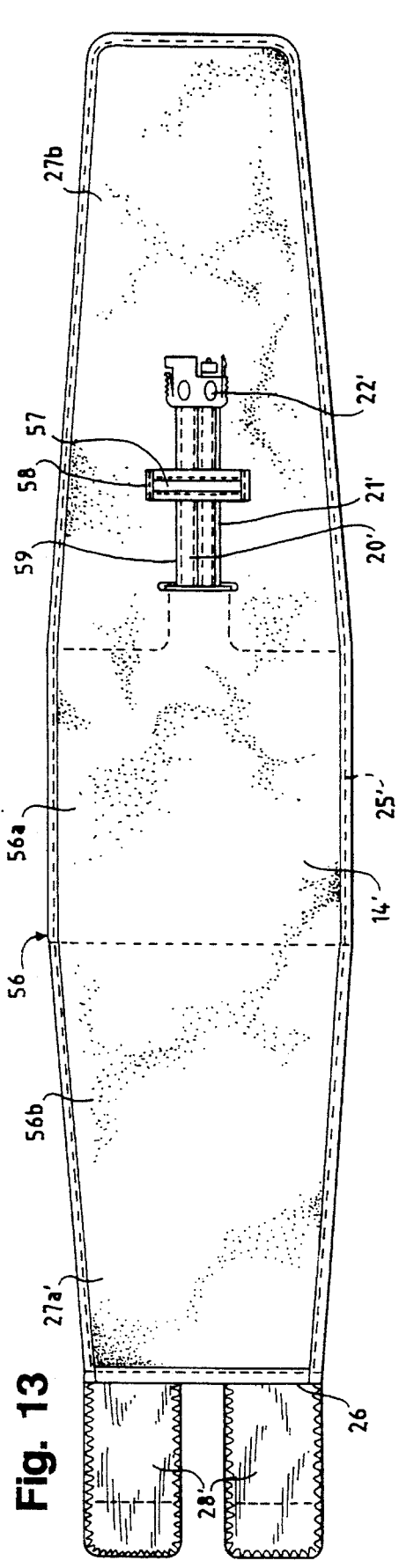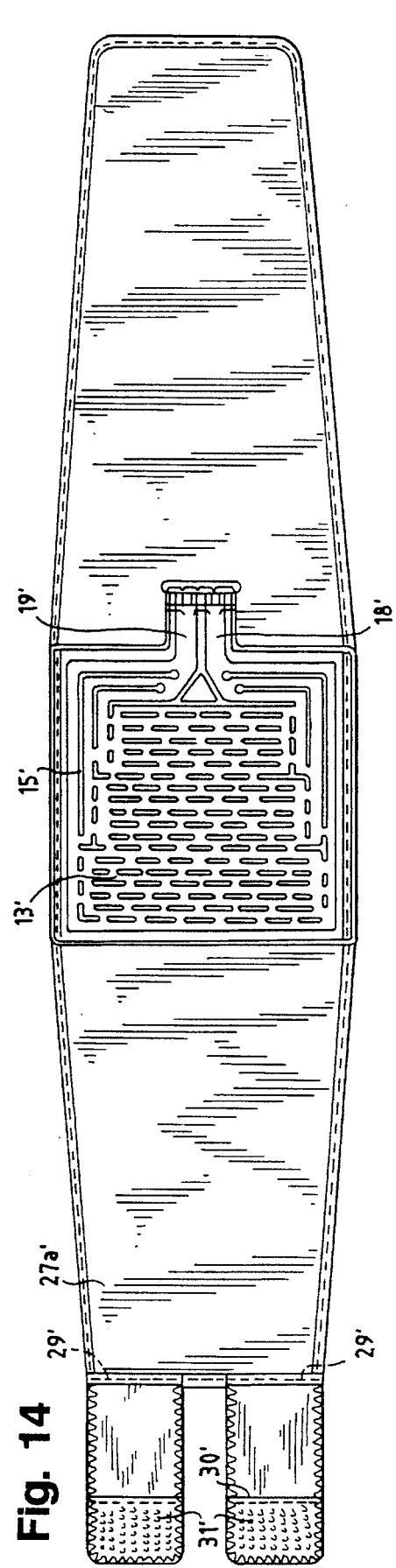

THERMAL BLANKET WITH ELASTIC FIT

BACKGROUND AND SUMMARY

This application is a continuation-in-part of U.S. patent application Ser. No. 139,286, filed Oct. 20, 1993, now pending.

The therapeutic use of thermal blankets having walls of flexible polymeric material that are sealed together to define a labyrinth of passages for the circulation of heating or cooling fluid is well known. While such therapy may involve either heating or cooling portions of the body, it is the cooling mode that in recent years has received particular attention because of its effectiveness in post-operative treatment and in connection with physical therapy. In particular, cryotherapy following soft tissue trauma has been shown to reduce pain, swelling, blood loss, inflammation and hematoma formation. During the rehabilitative process, cryotherapy has been utilized effectively to diminish inflammation and patient discomfort.

For such therapy, the thermal blanket should fit snugly about and uniformly contact the area of the body requiring treatment. Where the treatment site is relatively flat, or is of regular contour, these objectives may be partially accomplished with a blanket that normally lies flat and can be placed against, or wrapped about, the body part. However, tightly wrapping a thermal blanket to a treatment area with Ace bandages or the like often results in the blanket having too tight of a fit when the treatment area is moved and may be unduly restrictive or uncomfortable for the patient. In situations in which the blanket is loosely wrapped to accommodate such limited body movement, effective thermal treatment is often hindered by the lack of a tight, compressive fit. Such objectives are also far more difficult to achieve when the body portion to receive thermal treatment is a joint area of complex and variable curvatures such as the shoulder, elbow, ankle or knee. In such a case, the inability of a flat blanket to assume double curvatures and follow complex body contours may seriously compromise the effectiveness of the intended treatment. An alternative approach, that of providing a pre-formed non-planar blanket sized and shaped to match the contour of the treatment site, is considered impractical for a number of reasons including manufacturing complexities and cost.

Effective cryotherapy therefore requires that the thermal blanket be maintained in a compressive relation with the treatment area and that the fit of the blanket should accommodate limited body movement while still maintaining that compressive relation. While problems with achieving such a compressive but elastic fit obviously occur in situations where a thermal blanket is applied to a curved or complex body area, such problems are also prevalent when treating relatively flat areas of the body like the lower back or hip area which expand and contract, respectively, with the patient's breathing or flexure of the covered muscles.

Accordingly, an important aspect of this invention lies in providing a blanket that is particularly suitable for compressive thermal treatment of flat or complex body areas while still accommodating limited body movement and being easily adjustable to fit patients of different size and physical characteristics notwithstanding the fact that the blanket is manufactured (and may be marketed and stored) in substantially flat or planar condition. In blanket constructions designed for use on joint or complex areas of the body, a zigzag arrangement of dual passages can extend through the blanket in directions that eliminate or greatly reduce possibilities of partial or total flow obstruction since, by reason of such arrangement, forces imposed on the passages when the blanket is properly folded or wrapped over a treatment site tend to be in the form of twisting rather than kinking forces. Kinking of inlet and outlet tubes and the inlet/outlet passages of the blanket with which they communicate may also be prevented by providing the blanket with an integral limb wrap that supports the tubes and the fluid coupling element(s) connected to them and immobilizes such tubes and element(s) in relation to the patient's limb. The blanket may also be of the type in which a generally open passageway is provided without clearly-defined flow routes and such blankets may be used to treat flatter areas of the body (hand/wrist, back, and hip) for which the above kinking problems are not normally expected to occur.

Close fitting of the blanket to the treatment site is assured by providing the planar blanket with an outline of distinctive and developed shape, by utilizing Velcro-type hook and loop attachment means, and by providing substantially the entire outer (exterior) panel of the blanket with a soft loop-providing pile fabric which constitutes the loop component of the hook-loop attachment system. The hook means of the attachment system is provided on the bodyside-facing surface of at least one attachment patch which projects beyond a free edge at a first end of the blanket and which is elastically stretchable in a direction towards and away from that edge. The attachment patch is stretched during application of the blanket so that the hook-providing fabric connects with the external surface of the blanket at a generally opposite second end of the blanket to maintain the blanket in a tensioned and compressed, but expandable and contractible, relation about a body area for thermal treatment thereof.

Briefly, the blanket includes a foldable bodyside panel composed of double layers of thermoplastic sheet material heat-sealed together to define at least one, and preferably two, serpentine flow passages extending along zigzag pathways from an inlet opening to an adjacent outlet opening. The blanket may also be of the type that provides a generally open passageway between the inlet and outlet. The blanket includes a soft, foldable exterior panel covering the entire bodyside panel with the peripheral edges of the two panels being secured together. As stated, the entire exterior surface of the blanket is composed of a loop-providing pile fabric and at least one hook-providing elastic attachment patch extends from a free edge at a first end of the blanket for releasable attachment to the loop-providing exterior panel at a generally opposite second end of the blanket to ensure a snug fit over and about the treatment area.

When the blanket is configured for thermal treatment of a shoulder joint, it has a generally C-shaped outline that defines two main sections, one of which is intended to be folded over the top of the shoulder and the other about the shoulder's side (or uppermost arm) surface. A free edge of the second section is adjustably connected to the first section in partial overlapping relation by means of the hook-providing attachment patch which is elastically stretchable in directions towards and away from that free edge. The shoulder blanket also includes flap portions which cover portions of the back and chest of the wearer and are adjustably connected by a body strap which extends about the wearer's body below the shoulder and arm opposite from the shoulder receiving thermal treatment. Additional means in the form of resilient foam pads and closure flaps ensure close conformity of the blanket with the shoulder and promote more efficient and uniform thermal exchange.

When the blanket is configured for thermal treatment of generally flat body areas such as the hand/wrist, it may have a generally rectangular section that terminates in an integral tapered neck portion and two integral leg portions which extend in a transverse direction from said rectangular section for encircling the body area that is to receive thermal treatment. Each of the integral leg portions terminates in a free edge at a first free end of the blanket and is provided with at least one elastic attachment patch which projects beyond that free edge. The attachment patches are provided on their bodyside-facing surface with strips of hook-providing fabric for attachment to the blanket's external cover at a generally opposite second free end of the blanket when the blanket is worn. In use, the attachment patches are maintained in a slightly stretched condition to keep the blanket under a state of tension and provide a compressive fit. The stretchability of the patches ensures a snug fit about the treatment area while still accommodating limited movement of the treatment area without the fit of the blanket becoming unduly restrictive or tight. The attachment patches are composed of a material capable of 200% to 800% elastic elongation, preferably 500% to 700%, so that the patches provide such a tensioned but stretchable fit. In the preferred construction, the inlet and outlet tubes that communicate with the bodyside panel extend along the bodyside surface of the integral neck portion and a band of fabric is secured over those tubes to maintain the tubes in a parallel relation and prevent kinking or twisting thereof.

When the blanket is configured for thermal treatment of a knee, it may have an irregular, generally inverted, U-shaped central portion which has an upper base portion, a first dependent leg and a second dependent leg which together define a patella opening. Two upper leg-encircling portions extend in opposite directions from the upper base portion and two lower leg-encircling portions each respectively extending in opposite directions from the dependent legs. The upper leg-encircling portions are generally longer than the lower leg-encircling portions to encircle the generally greater circumference of the patient's upper leg directly above the kneecap. At least one elastic attachment patch is provided on one of the upper leg-encircling portions and on one of the lower leg-encircling portions for attachment to the respective other leg-encircling portion when the blanket is secured about a patient's knee. The elasticity of the attachment patches provides a snug compressive fit but still allows the patient limited movement of the knee area without hindering that compressive fit or causing discomfort to the patient.

The thermal blanket may also be configured for administering thermal treatment to generally larger body areas of regular contour such as the back or hip area. In such a construction, the blanket is generally defined by a four-sided central section and two wrapping portions that extend from opposite ends of the central portion. One of the wrapping portions is provided at its free end with at least one elastic attachment patch which projects beyond that free end for interlocking attachment with the external surface of the other wrapping portion when the blanket is worn. Most advantageously, the inlet and outlet tubes that communicate with the bodyside panel may extend along one of the wrapping portions and a band of fabric may be secured over those tubes for maintaining the tubes in a parallel relation and preventing twisting and kinking thereof.

Other features, advantages and objects will appear from the specification and drawings.

DRAWINGS

FIG. 1 is a top plan view of a shoulder blanket embodying the invention.

FIG. 2 is a plan view of the underside of the shoulder blanket.

FIG. 3 is a fragmentary view, taken partly in section and in exploded condition, showing the inlet/outlet tube arrangement and coupling element of the blanket.

FIG. 13 is a top plan view of a hip or back blanket embodying the invention.

FIG. 14 is a plan view of the underside of the hip or back blanket.

DETAILED DESCRIPTION OF PREFERRED EMBODIMENT

Figure 4:
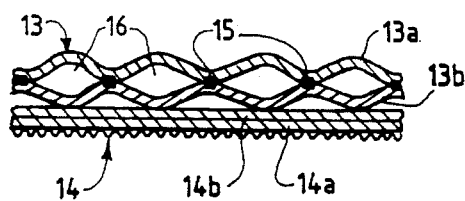
FIG. 4 is an enlarged and somewhat schematic sectional view taken along line 4—4 of FIG. 2.

Referring to FIGS. 1–6, the numeral 10 generally designates a fluid-circulating thermal blanket for post-operative treatment of a joint area of the body. The particular blanket shown in FIGS. 1–6 is designed specifically for the post-operative treatment of the shoulder area; however, many of the important features described hereinafter are also suitable for use on blankets shaped to be wrapped over or about other body areas such as the hand/wrist, knee, back, hip, elbow, and ankle. Some of such blanket configurations are illustrated in FIGS. 7–14.

The shoulder blanket shown in FIGS. 1–6, as well as the blankets shown in FIGS. 7–14, may be laid flat and are manufactured in planar condition, a feature most advantageous from the standpoint of manufacturing efficiency and purchaser cost. The shoulder blanket's outline is of distinctive and irregular shape and generally defines two main sections 10a and 10b arranged in a generally C-shaped configuration, a T-shaped limb-wrapping section 10c, and a pair of integral flap portions 11 and 12 which project outwardly from the first main section 10a.

The shoulder blanket is generally composed of two panels: a bodyside or inner panel 13 and an exterior or outer panel 14. As shown most clearly in FIG. 4, the bodyside panel is substantially non-stretchable and composed of double layers 13a and 13b of thin, flexible thermoplastic sheet material joined together along heat seal zones 15 to define at least one, and preferably two, serpentine fluid flow passages 16 and 17 leading from a single inlet 18 to a single outlet 19 (FIG. 2). Flexible inlet and outlet tubes 20 and 21 are sealed to and communicate with inlet 18 and outlet 19, respectively, and the opposite ends of the tubes are joined to a fluid coupling element 22 for operatively connecting the blanket to the equipment 23 that circulates the water or other thermal fluid and cools (or heats) that fluid to a selected temperature for circulation through the passages of the blanket. Most advantageously, the coupling element 22 is of the self-sealing, quick-disconnect hermaphroditic type as disclosed in detail in co-owned patents U.S. Pat. Nos. 4,982,736 and 4,951,665, the disclosures of which are incorporated by reference herein. A flow restrictor in the form of a tubular insert 24 having a reduced flow passage is located in outlet tube 21 (or in the adjacent fitting of coupling element 22) for back-pressuring the passages of the blanket for maintaining them in fluid-filled condition during use.

Referring to FIGS. 2 and 3, it will be observed that the serpentine passages 16 and 17 extend in approximately the same directions through substantially the entire area of bodyside panel 13 but each such passage has a separate zigzag configuration that promotes thermal transfer and, at the same time, reduces the possibility that folding of the blanket in normal use might result in kinking and flow obstruction. For example, referring to FIG. 3, passage 17 extends back and forth in a pattern characterized by relatively long tubular leg portions 17a alternately extending in reverse directions and connected by relatively short tubular connecting portions 17b. The same observation applies to the relatively long tubular leg portions 16a and relatively short tubular connecting portions 16b of adjacent flow passage 16. The pattern is a developed one with the relatively long tubular portions 16a and 17a extending in the direction of expected folding of that portion of the blanket through which they pass, and with the relatively short tubular connecting portions 16b and 17b generally traversing the directions of such folds. The result is that normal folding of the blanket is unlikely to result in obstruction of either passage 16, 17 because the folding action tends to be accommodated by a slight torsional or twisting action of the longer tubular leg portions 16a and 17a and the folding of a blanket in normal use is not abrupt enough to result in kinking of the relatively short connecting portions 16b and 17b, partly because of their small size in relation to the radius of the fold and partly because their reduced dimensions coupled with their compound curves provides them with increased stiffness and resistance to kinking. However, if localized forces should somehow be applied to one of the passages 16 or 17 while the blanket is in use, the companion passage may still circulate thermal fluid throughout the blanket and thereby avoid interruption of thermal treatment.

Exterior panel 14 of the blanket has an outline similar to that of bodyside panel 13 with the edges of the two panels secured together by stitching 25 or by other suitable attachment means. The exterior panel is substantially non-stretchable and formed of soft, insulating, easily-foldable fabric or other suitable sheet material. Of particular importance is the fact that its entire outer surface is composed of a loop-providing pile capable of releasably interlocking with Velcro-type nylon hook-providing patches. The fabric of the exterior panel may be multiple-layered as indicated in FIG. 4, with one layer 14a being composed of nylon loop-providing fabric and the other layer 14b being of a soft thermally-insulating material such as a closed-cell polyester foam backed by nylon jersey. Effective results have been obtained using a nylon loop fabric with polyester foam core and nylon jersey backing marketed under the "TEMPO" trademark by Lockfast, Cincinnati, Ohio, but other materials having similar properties are commercially available and may be used.

Figure 6:
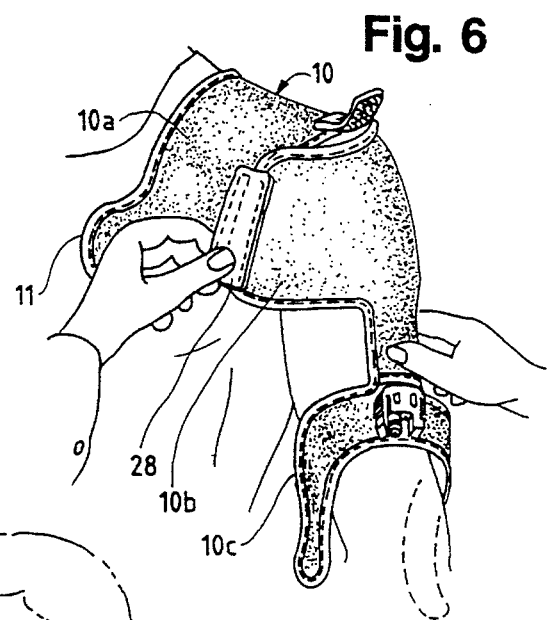
FIG. 6 is a perspective view illustrating the shoulder blanket being fitted upon a patient.

The first and second sections 10a and 10b of blanket 10 are arranged in a generally C-shaped configuration with the second section terminating in a substantially straight edge 26 at its first free end 27. An attachment patch 28 is secured to free end 27a by stitching 29 or by any other suitable means and, as shown clearly in FIGS. 1 and 2, projects well beyond edge 26. The rectangular patch is ideally formed of stretchable elastic fabric with directions of stretch and recovery extending at right angles to edge 26. Along its bodyside surface, the attachment patch is provided with a strip 30 of hook-providing fabric 31. The hooks of the Velcro-type fabric interlock with the loop pile on first section 10a at a generally opposite or opposed second free end 27b of the blanket when the patch 28 and end portion 27 are brought into overlapping relation with the first section in the manner depicted in FIGS. 5 and 6. Since almost the entire exterior surface of the blanket is formed of such loop pile fabric, it is believed that a wide range of adjustment is possible simply by varying the extent of overlap to bring the blanket into snug fitting relation over and about a patient's shoulder. When the blanket is properly fitted, section 10a extends over the top of the shoulder and section 10b wraps about the side of the shoulder (FIG. 6).

The elasticity of the fabric patch 28 helps ensure a snug fit of the blanket about a patient's shoulder, with the patch preferably being in a slightly stretched condition to maintain the blanket under a state of tension. The stretchability of the patch accommodates limited movement of the joint and also reduces the possibility that sudden or extreme movement might result in unintentional detachment of the hook-providing patch from the loop pile surface of the blanket. Attachment patch 28 is composed of a material capable of 200% to 800% elastic elongation, preferably 500%–700%, which provides sufficient elasticity so that the blanket can be fitted upon the body joint in a tensioned and compressive relation while still providing sufficient stretchability to accommodate movement of the body without the fit of the blanket becoming unduly restrictive or tight. Elasticized fabrics having such properties are well known and widely available. Effective results have been obtained using two-way stretch fabrics formed of Antron nylon and Lycra and available under the designation "Second Skin Cloth" from Minnetonka Mills, Inc., Hopkins, Minn., but other elasticized fabrics having two-way stretch and complete return capabilities may be used.

Figure 5:
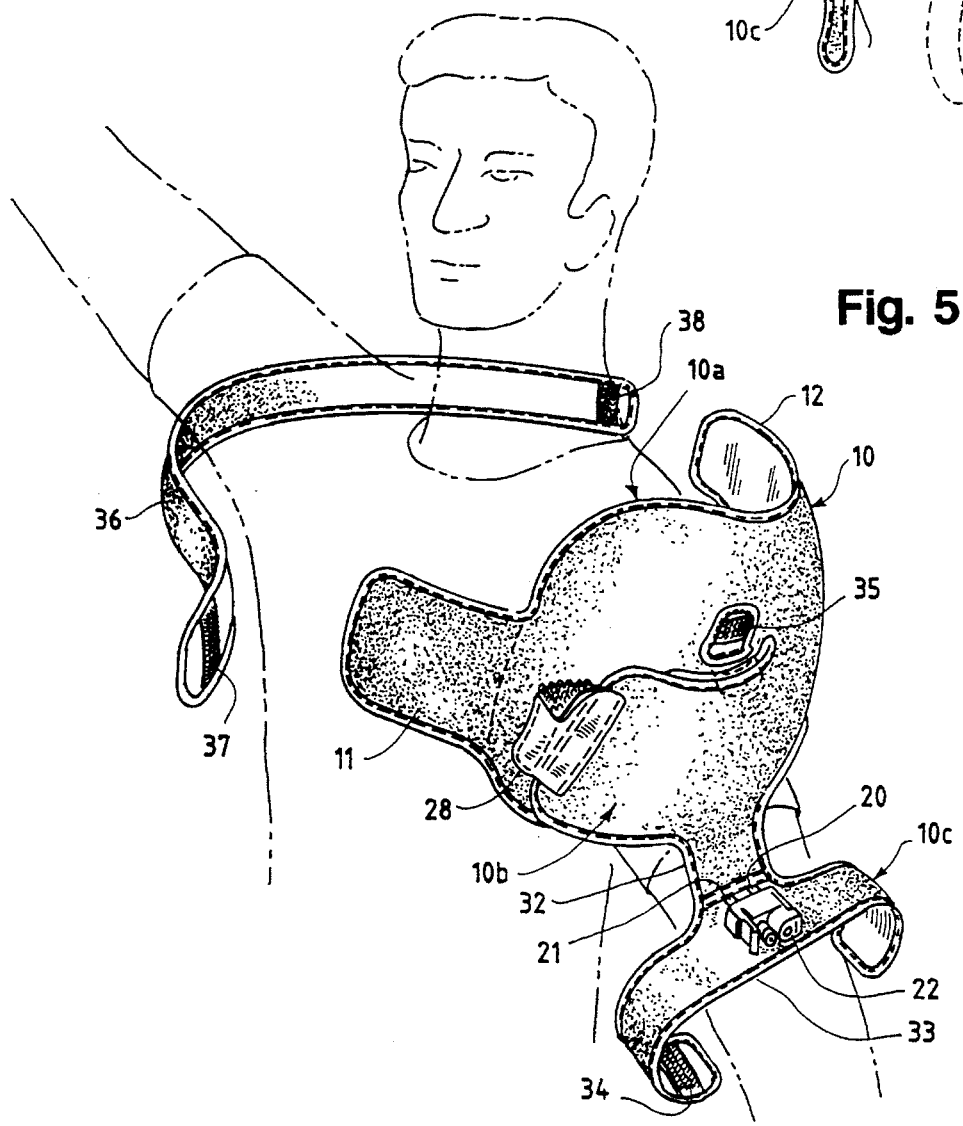
FIG. 5 is an exploded perspective view illustrating how the blanket would be fitted upon a patient's left shoulder.
Figure 7:
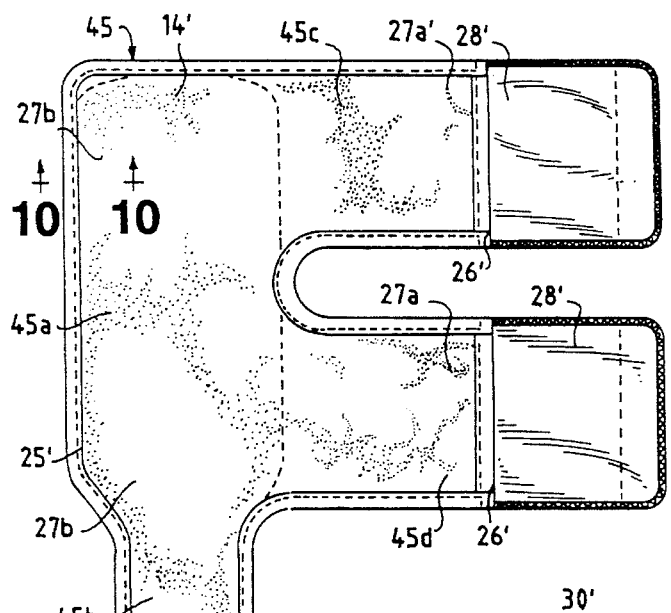
FIG. 7 is a top plan view of a generally rectangular flat blanket embodying the invention.

Limb-attachment section 10c is generally T-shaped in configuration, having a central strap portion 32 extending from the second section 10b of the blanket and terminating in an elongated band portion 33 extending at right angles to the strap portion. The T-shaped section 10c is preferably formed of double thicknesses of the same loop pile fabric as the outer panel 14 of the remainder of the blanket. Inlet and outlet tubes 20 and 21 extend through the strap portion and terminate at the band portion where they join with coupling element 22. As shown in FIGS. 1 and 5, the tubes 20, 21 exit from the strap portion at band portion 33 with coupling element 22 being located on the outside or exterior surface of the band portion. The fluid coupling element is therefor readily accessible for coupling to a mating element and, at the same time, the band portion prevents direct contact between element 22 and a wearer's arm.

At one of its ends, the band portion 33 is provided along its inside surface with a hook-providing fabric attachment patch 34. In use of the blanket, the band portion is wrapped about the patient's upper arm with patch 34 being brought into contact with the soft, loop pile outer surface of the band's other end portion to secure the fluid coupling element 22 about the patient's arm. Movement of the coupling element and twisting and possible kinking of tubes 20 and 21 are thereby effectively prevented.

One of the main sections of the blanket, section 10a in the embodiment illustrated, may be provided with a Velcro-type tab or flap 35 for engaging the loop pile surface of the other main section 10b along the corner of the patient's shoulder, thereby closing the small gap that might otherwise exist between the edges of sections 10a and 10b when the blanket is in place.

The flaps 11 and 12 which extend from blanket section 10a provide attachment areas for the ends of a body strap 36 that extend about the patient's upper torso beneath the arm opposite from the shoulder undergoing treatment. The body strap 36, shown most clearly in FIG. 5, may be composed of double thicknesses of the same loop pile fabric used for the exterior layers of blanket sections 10a and 10b. Hook-providing Velcro-type patches 37 and 38 are located at the ends of the body strap for engagement with soft pile outer surfaces of flaps 11 and 12 when the blanket is worn.

It has been found useful to interpose soft, resilient foam pads or cushions at certain locations between the inner and outer panels of the blanket to ensure that the passage-providing panel of the blanket will be maintained in good thermal exchange relation with areas of the shoulder where slight depressions commonly exist. Two such resilient foam pads 39 and 40 are provided between the panels of blanket section 10a as shown in FIG. 2. If desired, a resilient foam strip may also be interposed between the double thicknesses of the body strap 36.

Figure 8:
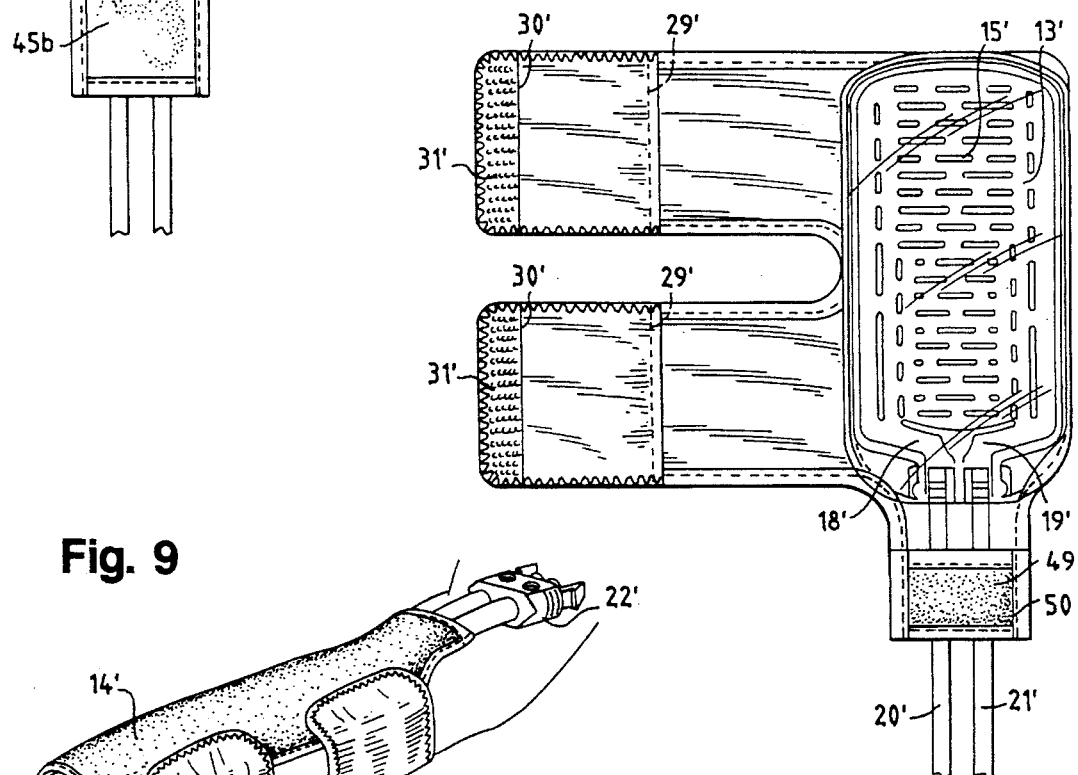
FIG. 8 is a plan view of the underside of the blanket illustrated in FIG. 7.
Figure 9:
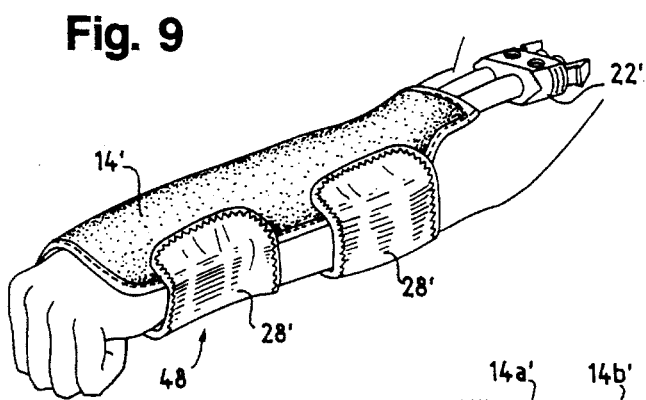
FIG. 9 is a perspective view illustrating how the blanket of FIGS. 7 and 8 would be fitted upon a patient's left hand/wrist.

The foregoing blanket construction may also be advantageously configured for application to other curved or flat areas of the body as exemplified by the blankets illustrated in FIGS. 7–14 in which like numerals designate like components. In FIGS. 7–10, the numeral 45 generally designates a fluid-circulating thermal blanket for thermal treatment of generally flat body areas such as the hand/wrist as shown in FIG. 9.

Blanket 45 is generally composed of two panels: a bodyside or inner panel 13' and an exterior or outer panel 14'. As shown most clearly in FIG. 10, the bodyside panel is composed of double layers 13a' and 13b' of thin, flexible thermoplastic sheet material joined together at a multiplicity of heat seal zones 15' that serve as baffles to provide a multiplicity of flow routes between the single inlet 18' and the single outlet 19' (FIG. 8). Flexible inlet and outlet tubes 20' and 21' are sealed to and communicate with inlets 18' and 19', respectively, and a fluid coupling element 22' is provided for connecting the blanket to fluid circulation equipment as hereinbefore described. In such a construction, inlet and outlet tubes 20' and 21' are preferably encased in a relatively thick layer of insulating foam (see FIG. 13) to protect the patient from direct contact with the tubes when thermal fluid is flowing therethrough, as well as to prevent thermal losses.

Figure 10:
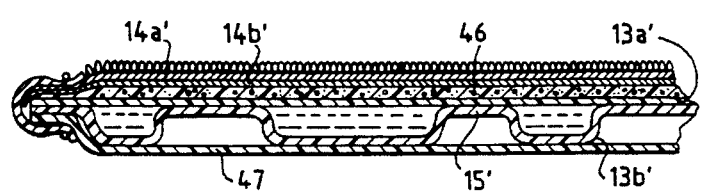
FIG. 10 is an enlarged and somewhat schematic sectional view taken along the line 10—10 of FIG. 7.

Exterior panel 14' of the blanket has an outline similar to that of bodyside panel 13' with the edges of the two panels secured together by stitching 25' or by other suitable attachment means. Exterior panel 14' can be comprised of two layers 14a' and 14b' as illustrated in FIG. 10 and hereinbefore described. A thin layer 46 of insulating foam may be interposed between bodyside panel 13' and exterior panel 14' to provide insulation and reduce thermal losses. The bodyside surface of panel 13' may also be provided with a thin layer of thermoplastic material 47 for covering heat seal portions 15' and providing a smooth surface on the side of the blanket that faces the patient.

Blanket 45 includes a generally rectangular section 45a that terminates in an integral tapered neck portion 45b. Two integral leg portions 45c and 45d extend in a transverse direction from one side of rectangular section 45a and each leg portion terminates in a substantially straight edge 26' at a first free end of the blanket 27a'. Attachment patches 28' are attached to edges 26' by stitching 29' or other suitable attachment means and project well beyond edges 26'. Along its bodyside surface, attachment patches 28' are provided with strips 30' of hook-providing fabric 31'. In use, as most clearly seen in FIG. 9, leg portions 45c and 45d are wrapped about the treatment area, in this case the hand/wrist area 48, and the hooks of the Velcro-type fabric on attachment patches 28 interlock with the loop pile on rectangular section 45a at a generally opposite or opposed second end 27b' of the blanket when patches 28' are brought into overlapping relation with rectangular section 45a. As stated, elastic patches 28' are composed of a material capable of 200% to 800% elastic elongation, preferably 500% to 700%, so that the blanket is maintained in tension during use while still accommodating limited movement of the treatment area.

Neck portion 45b is provided on its bodyside-facing surface with a strap 49 that is attached with stitching 50 or other suitable means to the blanket's outline and over inlet and outlet tubes 20' and 21'. Strap 49 hold tubes 20' and 21' in a parallel relation and prevents those tubes from twisting and kinking which could otherwise obstruct the flow of thermal fluid through the tubes and to inlet and outlet openings 18' and 19'.

Figure 11:
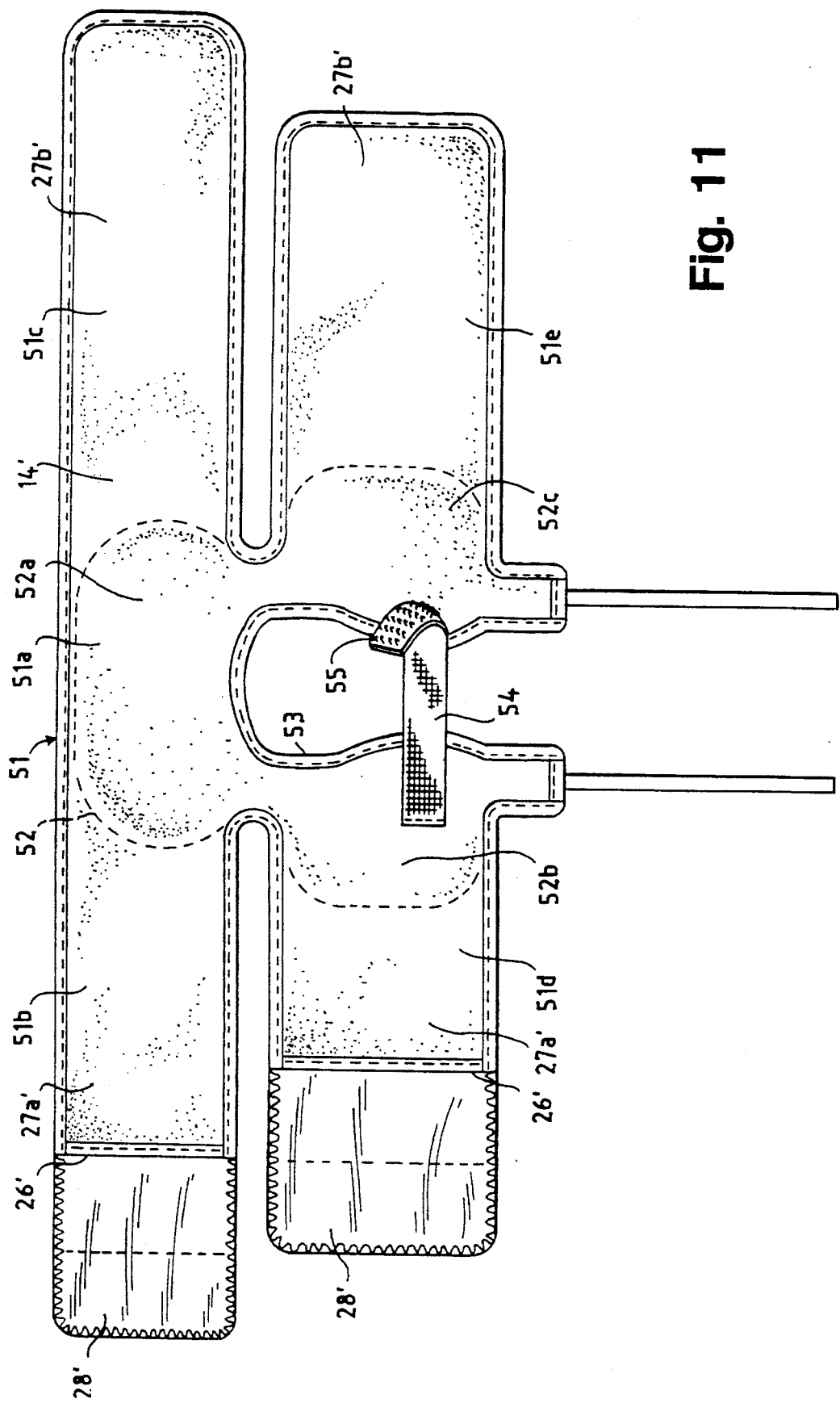
FIG. 11 is a top plan view of a knee blanket embodying the invention.
Figure 12:
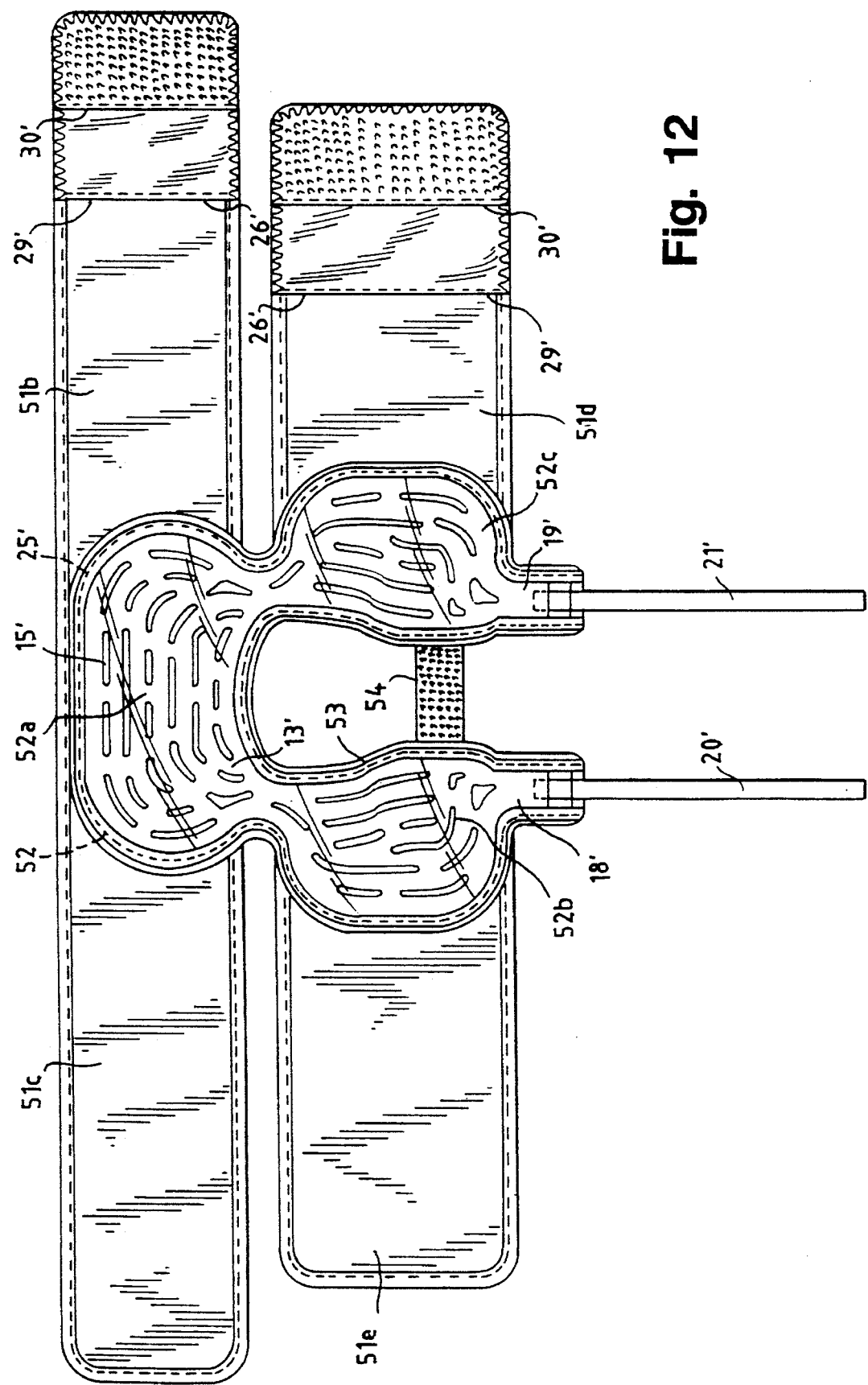
FIG. 12 is a plan view of the underside of the knee blanket.

Referring to FIGS. 11 and 12, the numeral 51 generally designates a thermal blanket configured for thermal treatment of the knee and which is particularly suitable for thermal treatment following orthoscopic surgery. Blanket 51 is generally composed of two panels: a bodyside or inner panel 13' and an exterior or outer panel 14". Most advantageously, blanket 51, bodyside panel 13", and exterior panel 14" have a construction similar to that hereinbefore described in connection with blanket 45.

Blanket 51 includes a central portion 51a and four leg-encircling extension portions 51b, 51c, 51d, and 51e. Central portion 51a includes an irregular, generally inverted, U-shaped section 52 that defines a patella opening 53. U-shaped section 52 includes an upper base portion 52a for placement over a patient's upper leg with opening 53 surrounding the patient's patella and two dependent leg portions 52b and 52c for covering portions of the knee directly adjacent to and beneath the patella. A strip 54 of hook-providing fabric 55 may be provided for attachment to the soft pile outer surfaces of dependent leg portions 52b and 52c to bring those portions into an overlapping relation directly beneath the patella when the blanket is worn.

Bodyside-facing panel 13" has the same general outline as irregular U-shaped section 52 and terminates at each of the dependent legs with a single inlet 18' and a single outlet 19' (FIG. 12). Inlet and outlet tubes 20' and 21' are respectively provided for communication with inlet 18' and outlet 19' and can be advantageously used with the coupling element hereinbefore described.

Upper leg-encircling portions 51b and 51c are generally longer than lower leg-encircling portions 51d and 51e so that they may accommodate the generally greater circumference of a patient's upper leg. Upper leg-encircling portions 51b and 51c each extend from upper base portion 52a of U-shaped section 52 in opposite directions and portion 51b includes a substantially straight free edge 26' at a first free end 27a' of the blanket. Similarly, lower leg-encircling portions 51d and 51e each respectively extend outward in opposite directions from dependent legs 52b and 52c with section 51d terminating with a free edge 26' at first end 27a' of the blanket. Each of the free edges 26' are provided with elastic attachment patches 28' as hereinbefore described. In use, opening 53 is centered about the patella and strip 54 of hook-providing fabric is used to bring dependent legs 52b and 52c into an overlapping relation to fully cover the knee area directly adjacent to and beneath the patella. Leg-encircling portions 51b and 51c are then wrapped about the patient's upper leg with portion 51b being brought into an overlapping relation with portion 51c. Similarly, leg-encircling portions 51d and 52e are wrapped about the patient's lower leg with portion 51d being brought into an overlapping relation with portion 51c. Attachment patches 28' are then stretched in tension so that hook-providing strips 30' are attached to the loop-providing outer surface of the blanket at generally opposite second free ends 27b' of the blanket on portions 51c and 51e. With attachment patches 28' in a such tensioned state, the blanket provides a compressive but elastic fit that allows limited movement of the patient's leg without compromising the compressive fit or causing the blanket to become unduly restrictive or uncomfortable.

Referring to another embodiment in FIGS. 13 and 14, the numeral 56 generally designates a thermal blanket that is useful for treating body areas of flatter or more regular contour such as the back, in which case the blanket is wrapped about the torso, or hip area, in which case the blanket is wrapped about a hip. Blanket 56 is generally composed of a bodyside-facing panel 13''' and an exterior or outer panel 14''' of the type hereinbefore described.

Blanket 56 includes a four-sided central portion 56a and extension wraps 56b and 56c which each respectively extend from opposite sides of central portion 56a. The size of rectangular portion 56a may be varied depending upon the particular application and the central portion will generally be larger for back applications than for hip treatment.

Extension wraps 56b and 56c have a generally trapezoidal shape extending outward from opposite ends of central portion 56a for encircling the area of the body adjacent to the treatment area. Wrap 56b terminates in a substantially straight edge 26' at a first free end 27a' of the blanket. At least one, and preferably two, attachment patches 28' are secured to free end 27a' by stitching 29' or by other suitable means. Along their bodyside surfaces, attachment patches 28' are provided with strips 30' of hook-providing fabric 31'. The hooks of the Velcro-type fabric interlock with the loop pile on wrap 56c at a generally opposite or opposed second free end 27b' of the blanket when patches 28' and wrap 56b are brought into an overlapping relation with wrap 56c. Free end 27a' may also be provided with a single attachment patch but it is believed that providing two attachment patches gives greater flexibility of fit and the space between the two patches also accommodates tubes 20' and 21' when the blanket is wrapped into a tight, generally circular, formation. As stated, attachment patches 28' are composed of an elastic material that is maintained in a slightly stretched condition when the blanket is worn. In such a case, the elasticity of fabric patches 28 maintains the blanket in a tensioned relation for effective thermal treatment while still allowing for limited body movement commonly associated with a patient's breathing when the blanket is wrapped about a patient's torso or with flexure of the covered muscles when the blanket is applied to a patient's hip area. Such a blanket configuration may also be useful for administering thermal treatment to body areas other than the hip or back by simply varying the proportions of central portion 56a and wrapping portions 56b and 56c.

Inlet and outlet tubes 20' and 21' are shown as being encased in a unitary layer of insulating foam 59 which prevents direct patient contact with tubes 20' and 21' through which thermal fluid flows and also prevents thermal losses. Forming foam 59 as a unitary piece also maintains the tubes in a parallel relation. In addition, tubes 20' and 21' preferably extend along wrapping portion 56c and a band of fabric material 57 is secured over those tubes by stitching 58 or other suitable means to further maintain the tubes in a parallel relation and to prevent twisting or kinking thereof.

While in the foregoing, embodiments of the invention have been disclosed in considerable detail for purposes of illustration, it will be understood by those skilled in the art that many of these details may be varied without departing from the spirit and scope of the invention.

We claim:

1. A thermal blanket for thermal treatment of areas of the body, comprising a foldable bodyside panel composed of double layers of thermoplastic sheet material heat-sealed together to define therebetween at least one passage communicating between an inlet opening and an adjacent outlet opening; and a soft, foldable exterior panel extending along said bodyside panel in parallel relation therewith; said bodyside and exterior panels being coplanar and having peripheral edges secured together with to form a unitary foldable blanket; said exterior panel having a soft loop-providing pile over substantially the entire exterior surface thereof; said blanket being provided with at least one attachment patch which projects beyond a free edge at a first end of said blanket and which is elastically stretchable in directions towards and away from said edge; said attachment patch having a bodyside-facing hook providing fabric for releasable attachment to said loop-providing pile of said exterior surface at a generally opposite second end of said blanket for maintaining said blanket in an interlocked but elastic relation about a body area for thermal treatment thereof; said blanket including a rectangular section which terminates in an integral tapered neck portion and two integral leg portions which extend in a transverse direction from said rectangular section, each of said leg portions having a free edge and being provided with at least one of said attachment patches which projects beyond said free edge; said blanket also including parallel and flexible inlet and outlet tubes extending along a bodyside-facing surface of said integral neck portion; said inlet and outlet tubes each being connected at one end to said inlet and outlet openings, respectively, and at their opposite ends to a fluid coupling element; said bodyside-facing surface of said neck portion being provided with a band of material that is secured over said inlet and outlet tubes to maintain said tubes in a parallel relation and prevent kinking and twisting thereof.

2. A thermal blanket for thermal treatment of areas of the body, comprising a foldable bodyside panel composed of double layers of thermoplastic sheet material heat-sealed together to define therebetween at least one passage communicating between an inlet opening and an adjacent outlet opening, and a soft, foldable exterior panel extending along said bodyside panel in parallel relation therewith: said bodyside and exterior panels being coplanar and having peripheral edges secured together to form a unitary foldable blanket; said exterior panel having soft loop-providing pile over substantially the entire exterior surface thereof; said blanket being provided with at least one attachment patch which projects beyond a free edge at a first end of said blanket and which is elastically stretchable in directions towards and away form said edge; said attachment patch having bodyside-facing hook-providing fabric for releasable attachment to said loop-providing pile of said exterior surface at a generally opposite second end of said blanket for maintaining said blanket in an interlocked but elastic relation about a body area for thermal treatment thereof; said blanket including an irregular, generally inverted, U-shaped central portion having an upper base portion, a first dependent leg and a second dependent leg which together define a patella opening; two upper leg-encircling portions extending in opposite directions from said base portion; and two lower leg-encircling portions each respectively extending in opposite directions from one of said dependent legs; said blanket being provided with at least two of said attachment patches which each respectively project beyond a free edge of one of said upper leg-encircling portions and one of said lower leg-encircling portions.

3. The blanket of claim 2 in which a strip of hook-providing fabric is provided for attachment to the loop-providing pile on said exterior surface of each of said dependent legs for bringing said dependent legs into an overlapping relation over the body area directly beneath a patient's patella.

4. A thermal blanket for thermal treatment of areas of the body, comprising a foldable bodyside panel composed of double layers of thermoplastic sheet material heat-sealed together to define therebetween at least one passage communicating between an inlet opening and an adjacent outlet opening; and a soft, foldable exterior panel extending along said bodyside panel in parallel relation therewith; said bodyside and exterior panels being coplanar and having peripheral edges secured together to form a unitary foldable blanket; said exterior panel having soft loop-providing pile over substantially the entire exterior surface thereof, said blanket being provided with at least one attachment patch which projects beyond a free edge at a first end of said blanket and which is elastically stretchable in directions towards and away from said edge; said attachment patch having a bodyside-facing hook-providing fabric for releasable attachment to said loop-providing pile of said exterior surface at a generally opposite end of said blanket for maintaining said blanket in an interlocked but elastic relation about a body area for thermal treatment thereof; said blanket including a four-sided central portion and two integral wrapping portions which each extend in opposite directions from said central portion, one of said wrapping portions being provided with at least one of said attachment patches projecting beyond a free edge thereof for interlocking connection with the external surface of the other of said wrapping portions; said blanket also including parallel and flexible inlet and outlet tubes extending along one of said wrapping portions; said inlet and outlet tubes being connected at one end to said inlet and outlet openings, respectively, and at their opposite ends to a fluid coupling element; said one of said wrapping portions being provided with a band of material secured over said inlet and outlet tubes for maintaining said tubes in a parallel relation and preventing twisting and kinking thereof.

5. The blanket of claim 1, 2 or 4 in which at least one pad of resilient foam is interposed between said panels in a selected area of said blanket for urging and maintaining said bodyside panel in said selected area in contact with a treatment area when said blanket is worn.

6. The blanket of claim 1, 2 or 4 in which said double layers of said thermoplastic sheet material are connected together at a multiplicity of heat seal points that do not provide a clearly defined flow path between said inlet opening and said outlet opening.

7. The blanket of claim 6 in which a thin layer of insulating foam is interposed between said panels to prevent thermal losses.

8. The blanket of claim 6 in which said bodyside panel is provided with a further layer of thermoplastic sheet material on a bodyside-facing surface thereof.

9. The blanket of claim 1, 2 or 4 in which said double layers of thermoplastic sheet material define therebetween at least one serpentine fluid-flow passage extending along a zigzag pathway from said inlet opening to said outlet opening.

* * * * *